(12) United States Patent
Heid

(10) Patent No.: US 8,094,785 B2
(45) Date of Patent: Jan. 10, 2012

(54) MODULATABLE RADIATION COLLIMATOR

(75) Inventor: Oliver Heid, Gunzenhausen (DE)

(73) Assignee: Siemens Aktiengesellschaft, Munich (DE)

( * ) Notice: Subject to any disclaimer, the term of this patent is extended or adjusted under 35 U.S.C. 154(b) by 87 days.

(21) Appl. No.: 12/612,166

(22) Filed: Nov. 4, 2009

(65) Prior Publication Data

US 2010/0061511 A1 Mar. 11, 2010

(30) Foreign Application Priority Data

Nov. 5, 2008 (DE) .......................... 10 2008 055 921

(51) Int. Cl.
*G21K 1/04* (2006.01)
*G21K 1/02* (2006.01)

(52) U.S. Cl. .......................... 378/151; 378/149; 378/150

(58) Field of Classification Search .................. 378/147, 378/149, 150, 151, 154, 156, 157, 158, 159
See application file for complete search history.

(56) References Cited

U.S. PATENT DOCUMENTS

| | | | | |
|---|---|---|---|---|
| 5,625,665 A * | 4/1997 | Fokkink et al. | ................ | 378/156 |
| 5,751,786 A * | 5/1998 | Welters et al. | ................ | 378/156 |
| 5,768,340 A * | 6/1998 | Geittner et al. | ................ | 378/159 |
| 6,061,426 A * | 5/2000 | Linders et al. | ................ | 378/149 |
| 6,118,855 A * | 9/2000 | Welters et al. | ................ | 378/158 |
| 6,188,749 B1 * | 2/2001 | Schiller et al. | ................ | 378/158 |
| 6,226,355 B1 * | 5/2001 | Prins | ............................. | 378/158 |
| 6,252,939 B1 * | 6/2001 | Young et al. | ................... | 378/156 |
| 6,370,228 B1 * | 4/2002 | Mockler et al. | ................ | 378/158 |
| 6,426,999 B2 * | 7/2002 | Prins | ............................. | 378/156 |
| 6,470,072 B1 * | 10/2002 | Johnson | ........................ | 378/154 |
| 7,209,547 B2 * | 4/2007 | Baier et al. | ..................... | 378/149 |
| 7,436,934 B2 * | 10/2008 | Hartick et al. | ................ | 378/150 |

FOREIGN PATENT DOCUMENTS

| DE | 10221634 A1 | 12/2003 |
|---|---|---|
| DE | 60018394 T2 | 12/2005 |

* cited by examiner

*Primary Examiner* — Allen C. Ho

(57) ABSTRACT

The invention specifies a radiation collimator, in particular an x-ray collimator, which can be arranged between a radiation source outputting radiation and an object. The radiation collimator includes absorber channels arranged adjacent to one another which form a two-dimensional collimator aperture in the form of a matrix and a first absorber element arranged in the absorber channel. The first absorber element blocks the radiation in a first position and allows the radiation at least partially through the absorber channel in at least one second position. The first absorber element is rod-shaped and can be moved in the absorber channel by a rotation about its longitudinal axis and/or by a longitudinal and/or transverse displacement from the first into the at least one second position. This is advantageous in that the two-dimensional collimator aperture can be modulated easily, rapidly and with high resolution.

11 Claims, 7 Drawing Sheets

MODULATABLE RADIATION COLLIMATOR

CROSS REFERENCE TO RELATED APPLICATIONS

This application claims priority of German application No. 10 2008 055 921.0 filed Nov. 5, 2008, which is incorporated by reference herein in its entirety.

FIELD OF THE INVENTION

The invention relates to a radiation collimator for use in beam therapy and to the use of a radiation collimator in radiation therapy.

BACKGROUND OF THE INVENTION

Radiation therapy is routinely used to treat invasive medical diseases such as cancer for instance. The principle behind beam therapy consists in an x-ray beam killing off cancerous cells. If the beam is directed at a cancer tissue or another abnormal area, the cells are destroyed. It is nevertheless unavoidable that the beam also damages healthy surrounding tissue. If the radiation is therefore not adequately restricted, the side effects for a patient can be serious.

A restriction of this type is usually achieved by collimating the beam, so that it only expands across the minimal required region so as to capture the whole cancer, but only a minimal region of the healthy surrounding tissue. Multileaf collimators are known for this purpose, with which leaves are inserted and/or removed into/from the beam so as to predeterminably change the shape of the developing beam.

The disadvantage of multileaf collimators is that the beam formation is restricted and undercut or hollow openings cannot be realized. Furthermore, the continuous beam inside the beam cannot be influenced, in other words a dose profile can only be influenced at the beam edge. Known types are also either very slow in adjusting the leaves or only allow two positions per leaf.

An improvement is achieved by the subject matter of DE 102 21 634 B4. The apparatus for spatial modulation of an x-ray beam bundle includes a plurality of flat attenuating elements for x-ray radiation, which are arranged on a support in the manner of a matrix and can be piezoelectrically pivoted or tilted independently of one another between at least two positions. For beam therapy, there is however often the desire to achieve a higher resolution of the matrix and to increase the modulation speed.

SUMMARY OF THE INVENTION

It is therefore the object of the invention to specify a beam collimator, the aperture of which has a higher resolution and can be quickly modulated.

According to the invention, the set object is achieved with the radiation collimator and with the use of the radiation collimator of claims.

The invention claims a radiation collimator which can be arranged between a radiation source outputting radiation and an object. It includes absorber channels arranged adjacent to one another which form a two-dimensional collimator aperture in the form of a matrix. It also includes at least a first absorber element arranged in the absorber channel. The first absorber element blocks and/or attenuates the radiation in a first position and allows the radiation to at least partially pass through the absorber channel in at least one second position. The first absorber elements are rod-shaped and can be changed in terms of position by rotation about their longitudinal axis and/or by a longitudinal and/or transverse displacement from the first into the at least second position. This is advantageous in that the two-dimensional collimator aperture can be modulated easily, rapidly and with high resolution.

In one development, radiation can pass through the absorber channel on the first absorber element to the object by moving the first absorber element in the radiation direction. This "pulling" forms a core shadow of the first absorber element and a hollow beam forms downstream of the collimator. This so-called "oscillation radiation" causes the surface dose to be reduced while maintaining the depth effect when irradiating a human body.

In a further embodiment, the first absorber elements can be embodied in the manner of a truncated pyramid or cone. A very high packing density is advantageous here.

Furthermore, the radiation collimator can include at least one second absorber element fixedly arranged in the absorber channel downstream and/or upstream of the first absorber element, with the position of the first absorber element relative to the second absorber element being changeable such that radiation can pass through the absorber channel in the at least one second position. This provides a realization with a high packing density and high modulation speed.

In an advantageous embodiment, the first and second absorber elements can be embodied in the manner of a truncated pyramid and are arranged so as to be displaceable in respect of each other.

The first and second absorber elements can also be arranged so as to be rotatable in respect of each other and are shaped in the manner of a truncated cone.

In one development of the invention, the collimator aperture can take the form of a partial surface of a surface of a sphere, which has a focal point of the radiation source as a central point. This ensures that maximum focused radiation can reach an object.

In a preferred embodiment, the absorber channels and the first and second absorber elements can taper in the direction of the radiation source. A curved collimator aperture can be formed as a result.

The beam collimator may also be an x-ray collimator for x-ray radiation.

The invention also claims a use of the inventive radiation collimator in an x-ray therapy apparatus. This is advantageous in that in the case of x-ray therapy, an aperture with high resolution which can be modulated quickly and easily can be used.

BRIEF DESCRIPTION OF THE DRAWINGS

Further details and advantages of the invention are apparent from the subsequent descriptions of several exemplary embodiments with reference to schematic drawings, in which.

DETAILED DESCRIPTION OF THE INVENTION

For reasons of clarity, the distances between webs 5 and the first and second absorber elements 3, 4 are in some cases shown in the FIGS. 1, 2 and 4 to 7. In one realization, these distances and/or "gaps" are not present. The first absorber elements 3 rest in a first position and the second absorber elements 4 always rest at least "tightly" against the webs 5. The first absorber elements 3 in the first position therefore do not allow radiation through the absorber channels 2.

Figure 1:
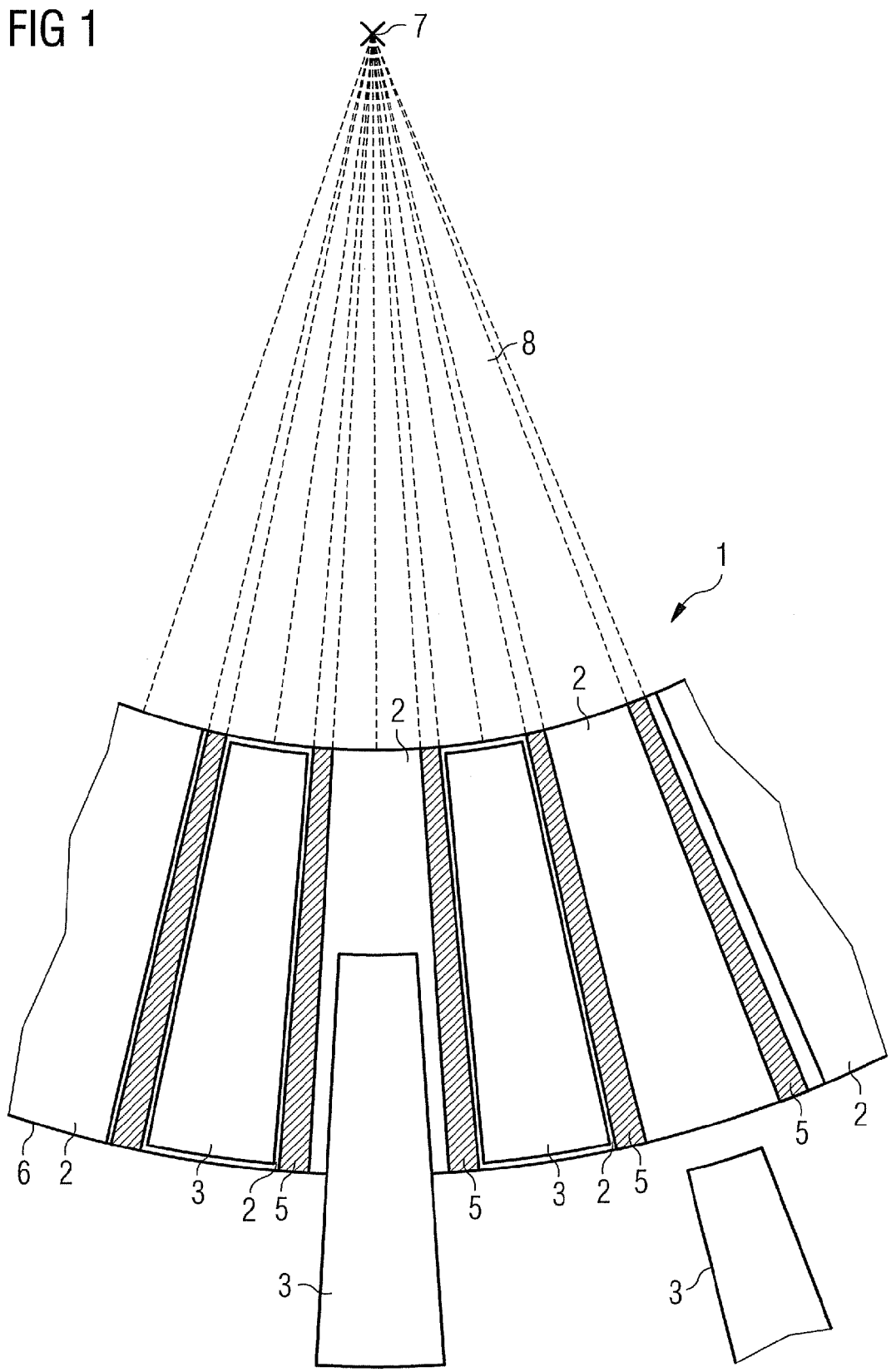
FIG. 1: shows a cross-section of a radiation collimator with moveable first absorber elements.

FIG. 1 shows an enlarged cutout from a radiation collimator 1 with a curved surface, which is arranged in the radiation field 8 of a radiation source 7. The object of the collimator 1 is to restrict, modulate and attenuate radiation. To this end, the collimator 1 forms a two-dimensional aperture, which can be modulated by the subject matter of the invention.

The radiation collimator 1 includes a support 6 with a plurality of absorber channels 2, which are directed at the focal point of the radiation source 7 and have a tapering form in the direction of the radiation source 7. The absorber channels 2 are restricted and/or formed by webs 5 in the support 6. Moveable rod-shaped first absorber elements 3 are mounted in the absorber channels 2, said absorber elements, in a first position, preventing the radiation from passing through the absorber channel 2 or only heavily attenuating the same. The first position of the first absorber element 3 is apparent in the first and third first absorber element 3 shown from the left. In a second position, which differs from the first position, the first absorber elements 3 allow the radiation to at least partially pass so that these can reach an object to be irradiated (not shown in FIG. 1). Different second positions of the first absorber element 3 are apparent in the second and fourth first absorber element 3 shown from the left. Radiation can therefore pass through the absorber channel 2 because the first absorber elements 3 have a tapering shape and when pulling the first absorber element 3 in the radiation direction form a gap between the webs 5 and the first absorber element 3. The first absorber elements can feature a truncated pyramid or cone shape. The first absorber elements 3 consist of a radiation-absorbing material, for instance tungsten, uranium or lead.

Figure 2:
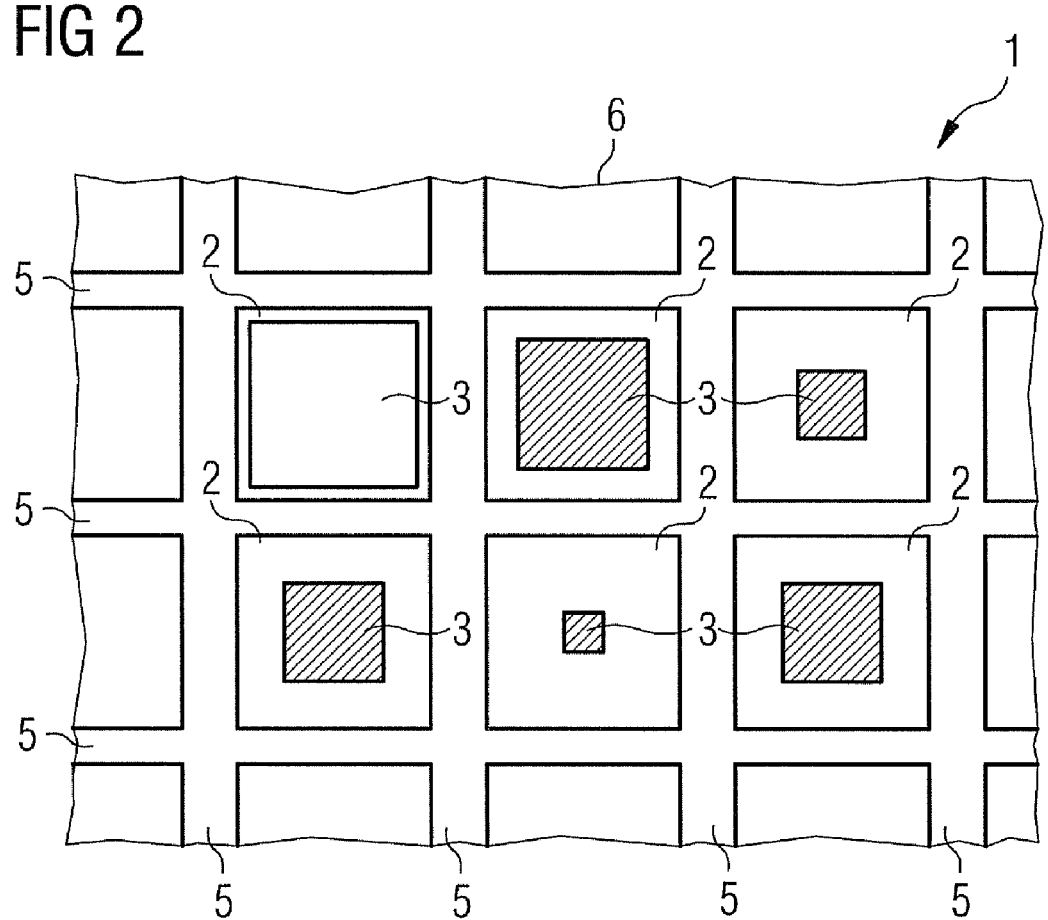
FIG. 2: shows a cross-section along a surface of a radiation collimator with moveable first absorber elements.

FIG. 2 shows a top view onto a part of a radiation collimator 1 in accordance with FIG. 1, with it being cut out along the surface. The cross-sections of the cutout first absorber elements 3 are, depending on their position—pulled/not pulled—visible with different sizes. Absorber channels 2 are formed by webs 5 in a support 6, in which absorber channels the first absorber elements 3 are moveably mounted.

Figure 3:
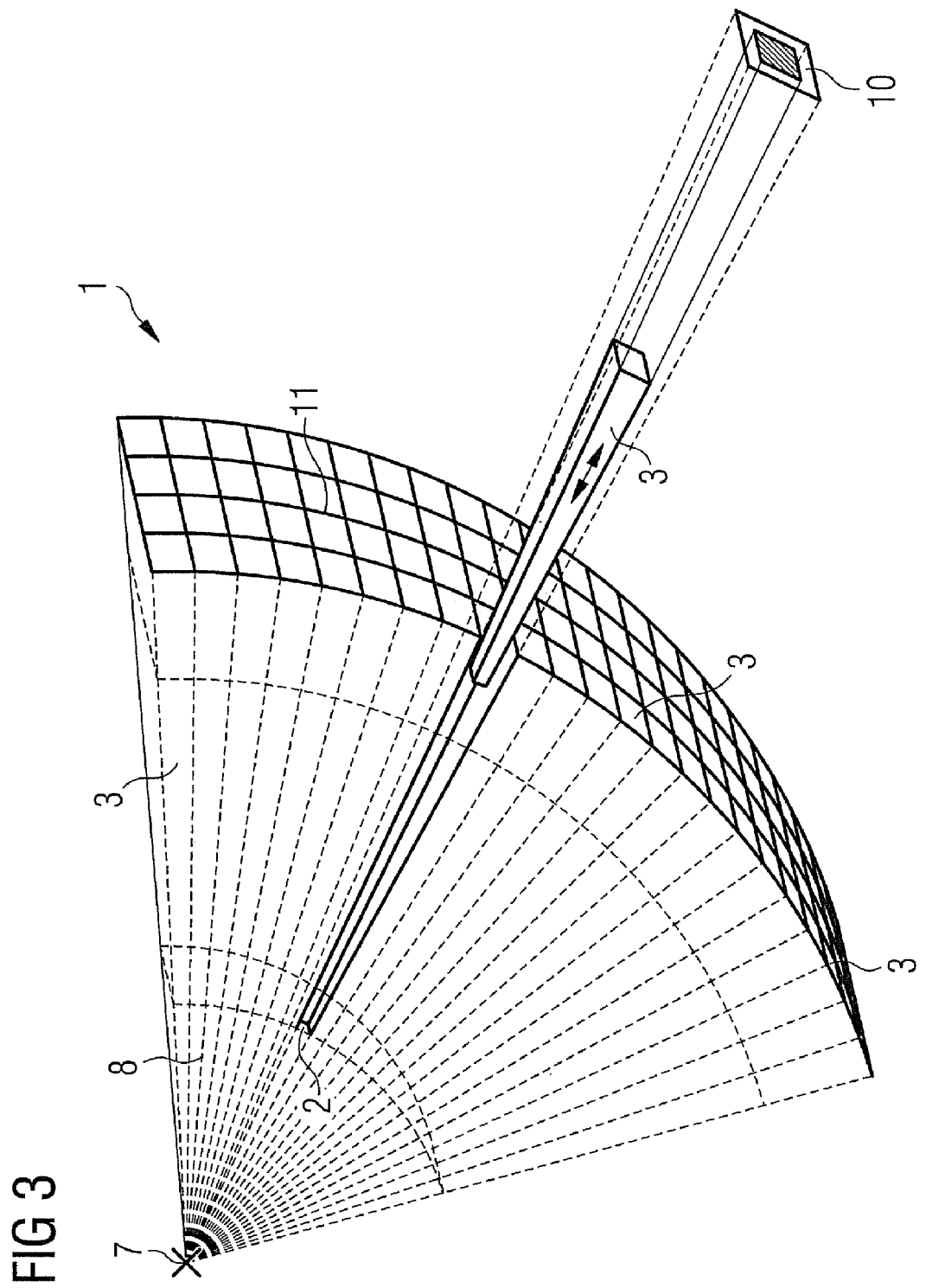
FIG. 3: shows a perspective view of a radiation collimator with moveable first absorber elements

To generate a high packing density, which forms a locally highly resolved aperture, the webs 5 may be very thin or even left out. FIG. 3 shows a perspective view of this embodiment. The absorber channels 2 are only formed by the bordering first absorber elements 3. The complete, tight packing of the rod-shaped first absorber elements 3 forms a two-dimensional collimator aperture 11 and blocks the radiation 8. If a first absorber element 3 is pulled from the packing away from the radiation source 7, an annular opening appears, the outer contour of which is formed by the non-pulled first absorber elements 3 and the inner contour of which is the shadow of the pulled first absorber element 3. A hollow beam 10 appears downstream of the collimator 1 as a result.

This pulling movement is kinematically simple, here linear, and only requires minimal force even at high pulling speeds. It is also favorable that as a result of the tapering form, for instance a conical shape, on the one hand in the first position, i.e. in the plugged-in state, a tight packing is generated, while on the other hand when pulling the first absorber element, a slight detachment from the adjacent absorber elements 3 takes place and the movement is thus friction-free.

A linear drive of the first absorber elements 3 can take place for instance by means of magnetic coils and magnets and/or iron cores attached to the first absorber elements 3 or by means of a piston effect and pressurized air, or by means of piezoelectric friction drives. The diverging axes of the first absorber elements 3 produce additional installation space for guiding tubes and actuators below the collimator 1, if necessary in the core shadow of the first absorber elements 3.

The cross-section of the first absorber elements 3 may generally be triangular, quadrangular or hexagonal for instance. Even with the narrowest of packing, round first absorber elements 3 require filling material for diminution of the residual openings. These stationary absorbers can be produced by boring a support 6 or formed by means of triangular or round rods.

The core shadow 10 of the first absorber elements 3 has an additional positive effect, since it effects a reduction in the surface dose without entailing disadvantages for the depth effect (so-called "oscillation radiation").

32*32 first absorber elements 3 are needed for a resolution of 1*1 cm$^2$ over 32*32 cm$^2$ in an irradiation plane. With a geometric distance ratio of collimator 1—source 7 relative to object-source 7 of 1:3, the diameters of the first absorber elements are approximately 3 mm. 10 cm long first absorber elements 3 are needed for a good absorption.

Figure 4:
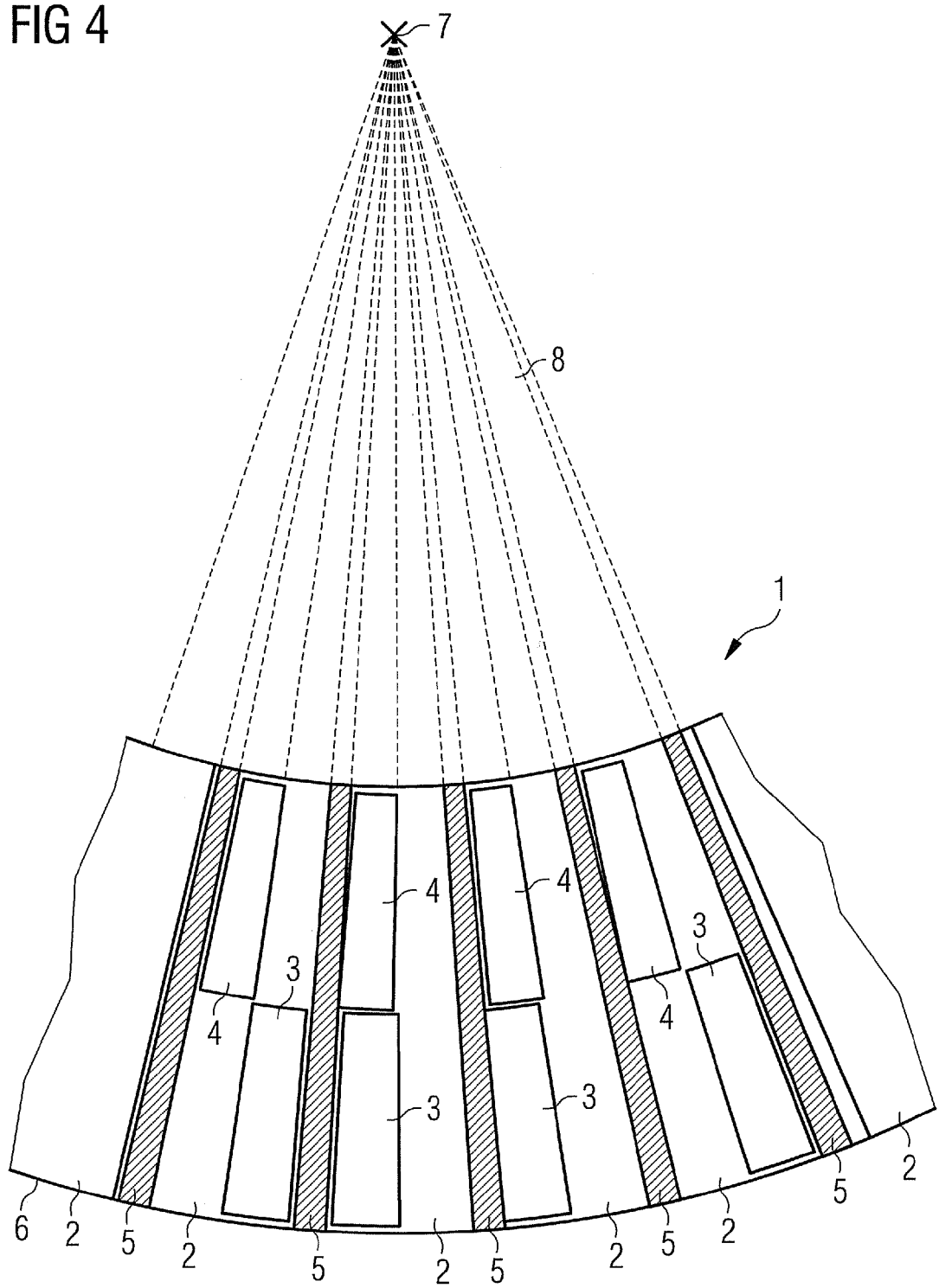
FIG. 4: shows a cross-section of a radiation collimator with second absorber elements and moveable first absorber elements.

FIG. 4 shows a further inventive embodiment. A cutout from a radiation collimator 1 with a curved surface is shown enlarged, the latter being arranged in the radiation field 8 of a radiation source 7. The object of the collimator 1 is to limit the radiation and to modulate and attenuate the same. To this end, the collimator 1 forms a two-dimensional aperture, which can be modulated by the subject matter of the invention. The radiation collimator 1 includes a support 6 with a plurality of absorber channels 2, which are aligned to the focal point of the radiation source 7 and have a tapering form in the direction of the radiation source. The absorber channels 2 are restricted and/or formed by webs 5 in the support 6. Second absorber elements 4 which approximately only fill half of the cross-section of the absorber channel 2 are fixedly arranged in the absorber channels 2. Moveable first absorber elements 3 are arranged downstream of the second absorber elements 4. They approximately only fill half of the cross-section of the absorber channel 2. The first and second absorber elements 3, 4 have the form of a truncated pyramid.

In a first position (see representation in the left and right absorber channel 2), the radiation is almost completely blocked by the first absorber element 3, whereas in a second position (see representation in the two middle absorber channels 2), radiation from the radiation source 7 can reach an object. Continuous displacement of the first absorber elements 3 allows the aperture to be easily modulated.

Figure 5:
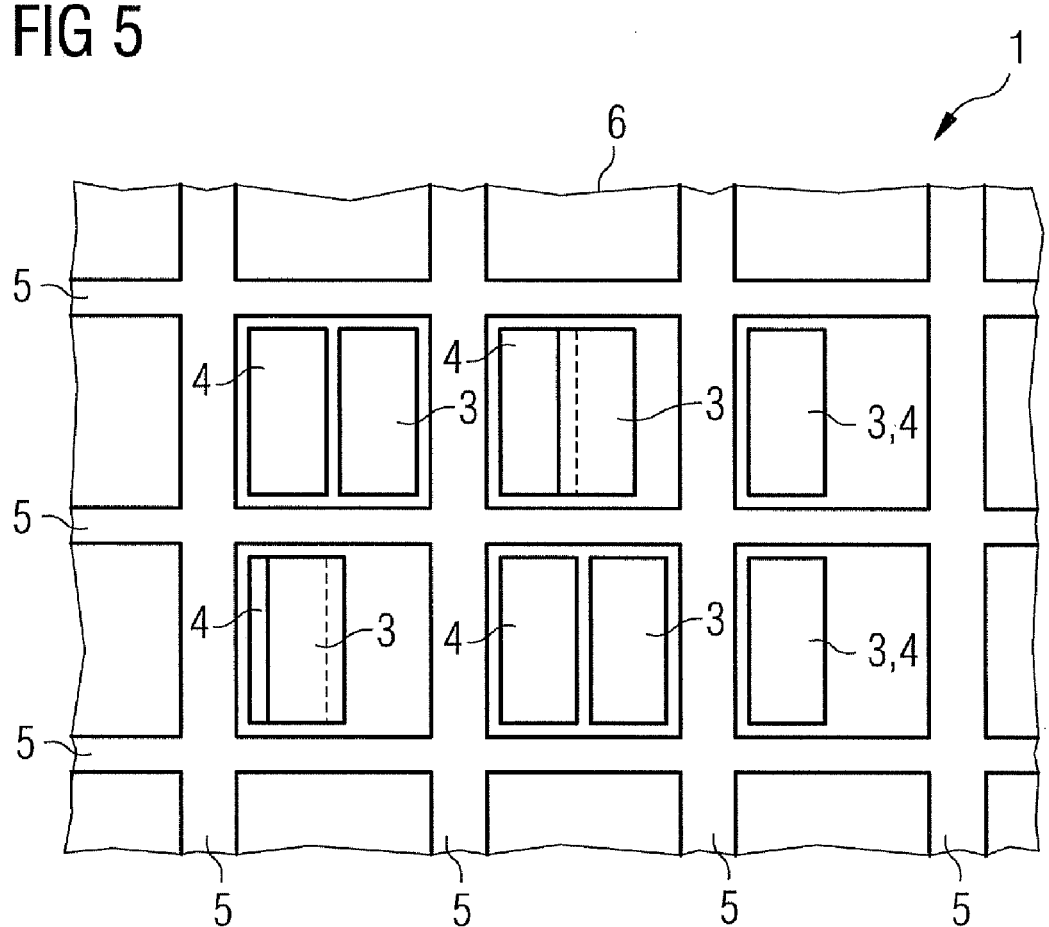
FIG. 5: shows a cross-section along a surface of a radiation collimator with second absorber elements and moveable first absorber elements.

FIG. 5 shows a top view onto a part of a radiation collimator 1 from FIG. 4. Absorber channels 2 are formed by webs 5 in a support, in which absorber channels first absorber elements 3 are moveably mounted. Second absorber elements 4 are also fixedly arranged in the channels 2. Displacing the first absorber elements 3 releases the openings of the absorber channels 2 so that radiation can pass through the first absorber elements 3. FIG. 5 shows first absorber elements 3 in different positions. The first and second absorber elements 3, 4 can be embodied in the manner of a truncated pyramid or in the form of a truncated cone segment.

Figure 6:
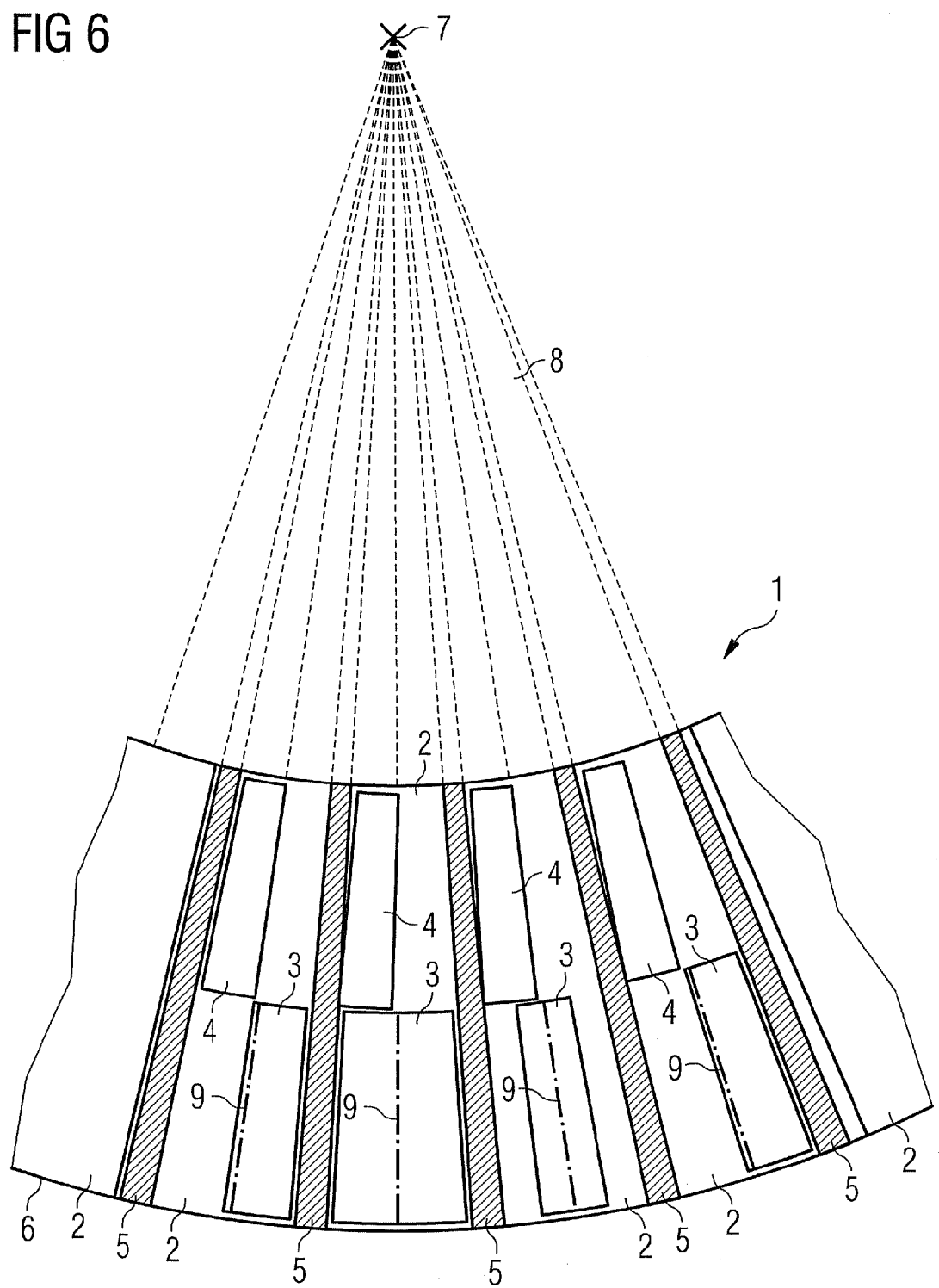
FIG. 6: shows a cross-section of a radiation collimator with second absorber elements and rotatable first absorber elements.

FIG. 6 shows a further inventive embodiment. One cutout from a radiation collimator 1 with a curved surface is shown enlarged, the latter being arranged in the radiation field 8 of a radiation source 7. The object of the collimator 1 is to restrict, modulate and also attenuate the radiation. To this end, the collimator 1 forms a two-dimensional aperture, which can be modulated by the subject matter of the invention. The radiation collimator 1 includes a support 6 with a plurality of absorber channels 2, which are directed at the focal point of the radiation source 7 and have a tapering shape in the direction of the radiation source 7. The absorber channels 2 are restricted and/or formed by webs 5 in the support 6. Second absorber elements 4 in the form of a half truncated cone, which approximately only fill the half cross-section of the absorber channels 2, are fixedly arranged in the absorber channels 2. Moveable first absorber elements 3, likewise in the form of a half truncated cone, are arranged downstream of the second absorber elements 4. They approximately only fill half of the cross-section of the absorber channel 2. In a first position (see representation in the left and right absorber channel 2), the radiation 8 is almost completely blocked by the first absorber element 3, while in a second position (see representation in the two middle absorber channels 2) radiation 8 from the radiation source 7 can reach an object. The continuous rotation of the first absorber elements 3 about the axis of rotation 9 enables the first absorber element 3 to be "rotated out" of the radiation and the aperture can thus be easily modulated.

Figure 7:
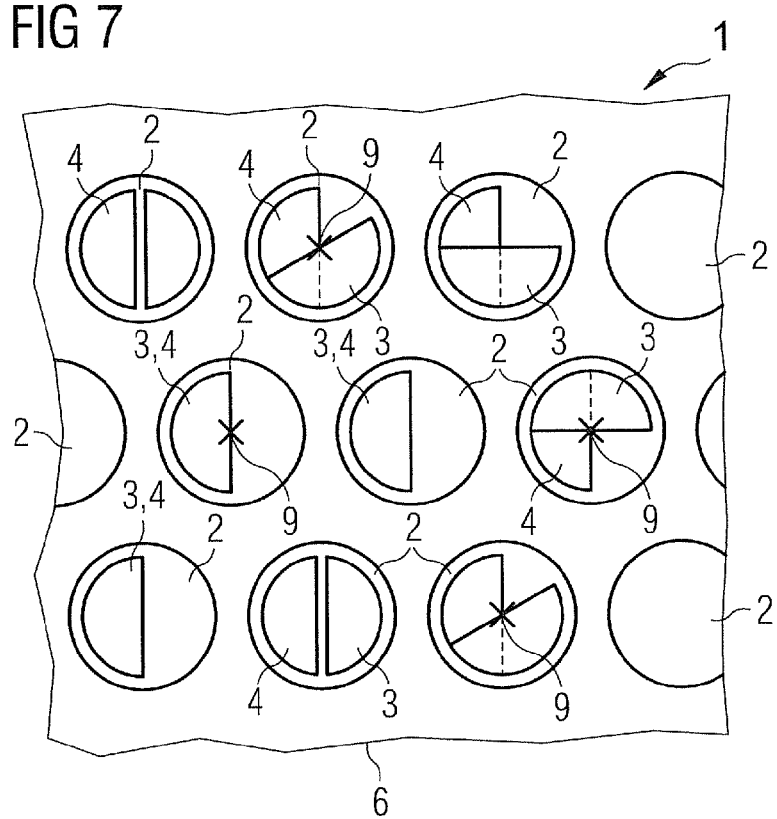
FIG. 7: shows a cross-section along a surface of a radiation collimator with second absorber elements and rotatable first absorber elements

FIG. 7 shows a top view onto a part of a radiation collimator 1 according to FIG. 6. Absorber channels 2 are formed by webs 5 in a support 6, in which absorber channels first absorber elements 3 are rotatably mounted about an axis of rotation 9. Second absorber elements 4 are also fixedly arranged in the channels 2. By rotating the first absorber elements 3 about the axes of rotation 9, the openings of the absorber channels 2 become larger so that radiation can pass through the first absorber elements 3. FIG. 7 shows the first absorber elements 3 in different positions. The first and second absorber elements 3, 4 are embodied in the form of a truncated cone segment.

Figure 8:
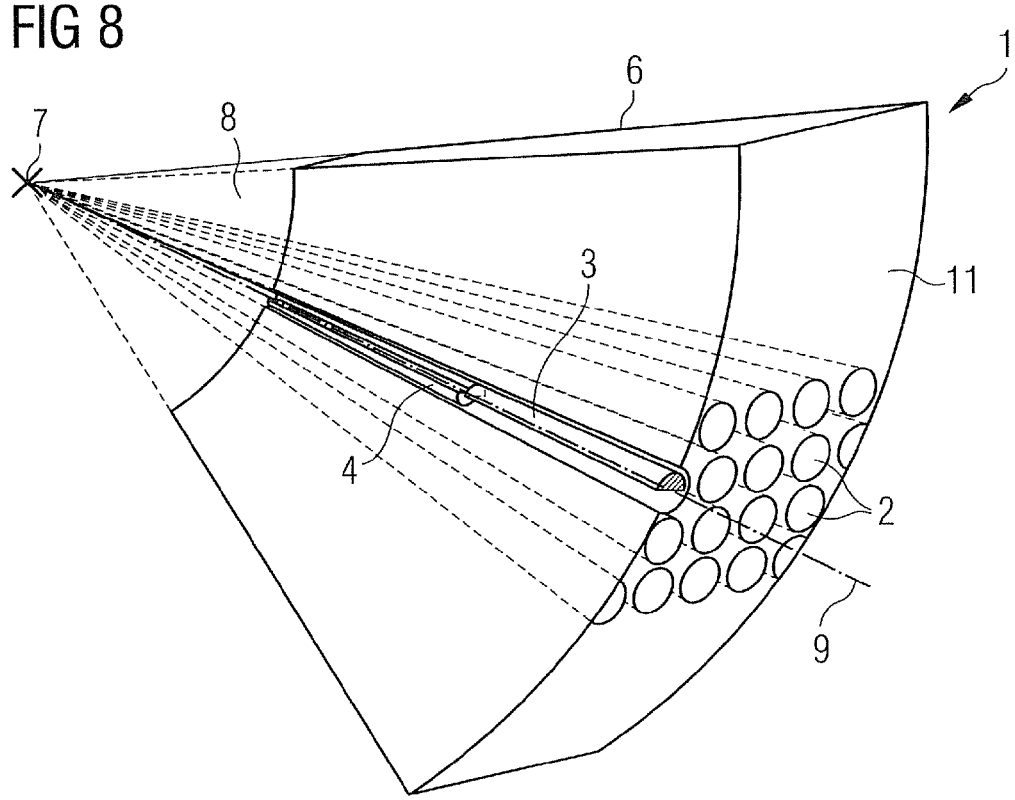
FIG. 8: shows a perspective view of a radiation collimator with second absorber elements and rotatable first absorber elements.

FIG. 8 shows a perspective view of the embodiment in FIGS. 6 and 7. A plurality of continuous, conically-running absorber channels 2, which are packed as tightly as possible, are located in a support 6 of a radiation collimator 1. The absorber channels 2 form a two-dimensional aperture 11, which can be modulated, by radiation 8 from a radiation source 8 being allowed to pass or blocked. To this end, rotatably mounted first absorber elements 3 are located in the absorber channels 2 along an axis of rotation 9. They take the form of a half truncated cone and block the radiation 8 in a first position and allow the radiation 8 to pass at least partially in at least a second position. As a counter element, an identically formed, fixed second absorber element 4 is located upstream of the first absorber element 3 in the absorber channel 2. The assigned solid angle region can thus be completely covered (no radiation) or released by up to 50%. The first absorber element 3 essentially moves in and out of the shadow of the second absorber element 4. An opening of the absorber channel 2 of more than 50% can be achieved by several rotatable smaller first absorber elements 3 arranged one behind the other. The very minimal rotation of the first absorber elements 3 required for the full modulation of the openings of the absorber channels 2 allows for a very high modulation speeds. Installation space for the actuators, for instance electromagnetic, piezoelectric or pneumatic, is available downstream of the radiation collimator 1.

The shadow of the first absorber elements 3 has an additional positive effect since it effects a reduction in the surface dose without entailing disadvantages for the depth effect (so-called "oscillation radiation").

32*32 first absorber elements 3 are required for a resolution of 1*1 $cm^2$ over 32*32 $cm^2$ in an irradiation plane. With a geometric distance radio of collimator 1—source 7 relative to object—source 7 of 1:3, the diameters of the first absorber elements are approximately 3 mm.

The radiation collimator 1 described in FIGS. 1 to 8 can preferably be used in x-ray apparatuses for a radiation therapy.

LIST OF REFERENCE CHARACTERS

1 Radiation collimator
2 Absorber channel
3 First absorber element
4 Second absorber element
5 Web
6 Support
7 Radiation source
8 Radiation
9 Axis of rotation
10 Hollow beam
11 Collimator aperture

What is claimed is:

1. A radiation collimator arranged between a radiation source and an object, comprising:
   a plurality of absorber channels that are arranged adjacent to one another;
   a plurality of first absorber elements arranged in the plurality of absorber channels that blocks a radiation emitted by the radiation source in a first position and passes the radiation through the absorber channels in a second position; and
   a two-dimensional collimator aperture that is formed by the plurality of first absorber elements arranged in the plurality of absorber channels;
   wherein the plurality of first absorber elements are each configured to be rod-shaped and to be moved in a respective absorber channel from the first position into the second position by a rotation of the respective first absorber element about a rotation axis aligned parallel to a longitudinal axis of the respective absorber channel;
   and wherein the plurality of first absorber elements are respectively shaped as a cone or a truncated pyramid.

2. The radiation collimator as claimed in claim 1, wherein the radiation reaches the object through the plurality of absorber channels by moving the plurality of first absorber elements in a radiation direction.

3. The radiation collimator as claimed in claim 1, further comprising a plurality of second absorber elements, wherein a respective second absorber element is fixedly arranged in the respective absorber channel downstream or upstream of the respective first absorber element.

4. The radiation collimator as claimed in claim 3, wherein the respective first absorber element and the respective second absorber element are displaceable arranged in respect of one another.

5. The radiation collimator as claimed in claim 3, wherein the respective first absorber element and the respective second absorber element are rotatable arranged in respect of one another.

6. The radiation collimator as claimed in claim 3, wherein the respective absorber channel and the respective first absorber element and the respective second absorber element taper in a direction of the radiation source.

7. The radiation collimator as claimed in claim 1, further comprising a plurality of second absorber elements, wherein a position of the respective first absorber element is changeable with a position of the respective second absorber element.

8. The radiation collimator as claimed in claim 1, wherein the collimator aperture has a partial surface of a surface of a sphere.

9. The radiation collimator as claimed in claim 8, wherein a central point of the collimator aperture is a focal point of the radiation source.

10. The radiation collimator as claimed in claim 1, wherein the radiation collimator is an x-ray collimator and the radiation is an x-ray radiation.

11. The radiation collimator as claimed in claim 1, wherein the radiation collimator is used in a radiation therapy apparatus.

\* \* \* \* \*